United States Patent
Bi et al.

(10) Patent No.: US 9,194,784 B1
(45) Date of Patent: Nov. 24, 2015

(54) HIGH PRESSURE, HIGH TEMPERATURE LUBRICITY TESTER

(76) Inventors: Hongfeng Bi, Houston, TX (US); Joseph Bi, Houston, TX (US); Rebecca Bi, Houston, TX (US)

(*) Notice: Subject to any disclaimer, the term of this patent is extended or adjusted under 35 U.S.C. 154(b) by 597 days.

(21) Appl. No.: 13/558,607

(22) Filed: Jul. 26, 2012

(51) Int. Cl.
*G01N 3/56* (2006.01)
*G01N 11/14* (2006.01)

(52) U.S. Cl.
CPC . *G01N 3/56* (2013.01); *G01N 11/14* (2013.01)

(58) Field of Classification Search
CPC ....... G01N 19/02; G01N 11/14; G01N 33/30; G01N 3/56; G01N 11/162; G01N 2011/002; G01N 2203/0019; G01N 11/165; G01N 11/167; G01N 11/142; G01N 2203/0021; G01N 2203/0025; G01N 2203/0026
USPC ........ 73/54.23, 54.28, 54.31–54.34, 53.05, 7, 73/9, 10
See application file for complete search history.

(56) References Cited

U.S. PATENT DOCUMENTS

| | | | |
|---|---|---|---|
| 2,001,861 A | 2/1933 | Almen | |
| 3,060,721 A | 10/1962 | Marsh et al. | |
| 3,136,150 A | 6/1964 | Young et al. | |
| 3,302,447 A * | 2/1967 | Mertwoy et al. | ................... 73/10 |
| 3,785,196 A * | 1/1974 | Smith | .......................... 73/53.05 |
| 3,913,377 A | 10/1975 | Lindeman | |
| 3,939,690 A * | 2/1976 | Kuss et al. | ........................... 73/9 |
| 4,458,528 A * | 7/1984 | Roper et al. | ............... 73/152.49 |
| 5,377,525 A | 1/1995 | Hutchinson et al. | |
| 5,388,442 A | 2/1995 | Kumar et al. | |
| 5,616,842 A | 4/1997 | Armengaud et al. | |
| 5,795,990 A | 8/1998 | Gitis et al. | |
| 6,105,415 A | 8/2000 | Kenney | |
| 6,112,573 A * | 9/2000 | Thelen | .............................. 73/10 |
| 6,330,820 B1 * | 12/2001 | Cotterill et al. | ...................... 73/9 |
| 6,418,776 B1 | 7/2002 | Gitis et al. | |
| 6,546,782 B1 | 4/2003 | De La Cruz et al. | |
| 6,752,001 B1 | 6/2004 | LaPointe | |
| 6,840,082 B2 | 1/2005 | Evans | |
| 7,013,713 B2 | 3/2006 | Webster et al. | |
| 2010/0126252 A1 * | 5/2010 | Bailey et al. | ................. 73/54.28 |

* cited by examiner

*Primary Examiner* — Daniel S Larkin
*Assistant Examiner* — Jamar Ray (57) ABSTRACT

A method and apparatus for monitoring lubricity consists of a cylindrical cell assembly (80) capable of withstanding high pressure and high temperature with a movable rotor (26) abrading a solid sample (28) while submerged in a liquid sample (74). A loading device (42) moves a bottom shaft (46) supporting the solid sample (28) as said solid sample (28) abrades and is moved upwards, and its movement is measured by a displacement sensor (40). Liquid sample (74) is drained through solid sample (28) into receiver (38) to measure filtration of solid sample (28). Heat is provided via a heater (64) and pressure is controlled via pressurization media (72).

15 Claims, 6 Drawing Sheets

HIGH PRESSURE, HIGH TEMPERATURE LUBRICITY TESTER

BACKGROUND

1. Field of Invention

The present invention relates to apparatuses and methods for monitoring, measuring, or analyzing the lubricity of fluid samples in conjunction with solid samples.

2. Description of Prior Art

U.S. Pat. No. 6,105,415 describes a method and apparatus for testing the lubricity of a drilling mud. The test is accomplished by rotating a core sample so that it rubs against a metal surface (simulating a rotating pipe or drill string in a well) and then saturating the core sample and the metal surface with a drilling mud. The energy required to rotate the core sample while it is saturated with the drilling mud is determined and this measurement is used to determine the lubricity of the drilling mud. This design is specifically intended to simulate downhole conditions, and requires both a drilling fluid sample and a core sample, with the core sample being positioned at only one angle. This limits the test parameters that can be specified to a relatively narrow range.

U.S. Pat. No. 3,060,721 describes an apparatus for testing lubricants by measuring the change in electrical resistance provided by wear or attrition of a test specimen. The apparatus of this invention provides an eccentric rotating surface and means for supporting a strip-like test specimen so that at least a portion of the periphery of said eccentric rotating surface bears against and rubs the test specimen, and induces cyclic tensile stresses therein. The test specimen and rotating surface are enclosed in a suitable vessel which is provided with inlet and outlet means, such that a controlled corrosive environment can be caused to exist within the vessel. Means are provided for continuously applying lubricant to the contact surface between the strap-like test specimen and the rotating surface. This apparatus does not, however, provide the means to measure lubricity. The user must employ microscopic measurement to examine the specimen in order to determine the amount of wear, the results of which determination can in turn can be used to calculate the lubricity of a tested fluid. Alternatively, the user may employ an electrical resistance test on the abraded surface of the specimen, should the specimen be made of conductive metal. The test procedures required to use this invention as intended are time-consuming and onerous, and this substantially limits the scope and usefulness of the invention.

U.S. Pat. No. 3,913,377 describes a friction testing machine in which fluids may be tested for lubricity. A disc, rotated continuously by a variable-speed driving means, has friction members clamped against its opposite faces by means of a calibrated, adjustable mechanism which controls the "normal" force holding the members against the disc. The friction force between the members and the disc may be determined by measuring the tangential force produced on the members as the disc rotates. One edge of the disc dips into a bath of the lubricant being tested, to provide lubricant at the juxtaposed disc and member surfaces. A heating means may be provided for the bath, to enable testing at elevated temperatures. While again limiting the testing apparatus to operating only at one angle, this device limits the possible specimen types which might make up the disk to only those which are of a sufficiently solid consistency.

It is an object of this invention to create a device which can measure the lubricity of a fluid submerging two solid samples of various kinds. At least one of the solid samples could be a porous media, and the filtration of said fluid through said porous media could also be measured under varying and controllable conditions, including but not limited to those of temperature and pressure.

SUMMARY OF THE PRESENT INVENTION

A lubricity tester in accord with the present invention is comprised of a cylindrical pressure cell wherein a solid sample is pushed against and abraded by a rotating rotor while being saturated and infiltrated by a liquid sample, all under conditions of temperature and pressure. The device is constructed so that pressure can be applied which forces the liquid sample to filter through the solid sample and out of the pressure cell. The solid sample is attached to a displacement sensor, which measures the movement of the solid sample as it is worn away by the rotor.

DRAWING FIGURES

Other objects, features and advantages will be apparent from the following detailed description of the preferred embodiment taken in conjunction with accompanying drawings in which.

REFERENCE NUMERALS IN DRAWINGS

8 Motor
8A Motor
8C Motor
10 Top shaft
10A Top shaft
10C Top shaft
12 Pressurization port
12A Pressurization port
12C Pressurization port
14 Bearing holder
14A Bearing holder
14C Bearing holder
16 Thread
16A Thread
16C Thread
18 O-ring
18A O-ring
18C O-ring
20 Sample cup
20A Sample cup
20C Sample cup
22 Thread
22A Thread
22C Thread
24 Hole
24C Hole
26 Rotor
26A Solid cone bit
26C Ring 27 Abrasive circular drill bit
27A Conical surface
28 Solid sample
28A Concave solid sample
28C Solid sample
29A Central hole
34 Valve
34A Valve
36 Tube
36A Tube
36B Tube
38 Receiver
38A Receiver
40 Displacement sensor
40A Displacement sensor
40C Displacement sensor
42 Loading device
42A Loading device
42C Loading device
44 Tube fitting
44A Tube fitting
46 Bottom shaft
46A Bottom shaft
46C Bottom shaft
48 Hole
48A Hole
50 O-ring
50A O-ring
50C O-ring
54 Thread
54A Thread
54C Thread
56 Sample holder
56A Sample holder
56C Sample holder
58 Thread
58A Thread
58C Thread
60 Retainer
60A Retainer
60C Retainer
61 O-ring
61A O-ring
62 Stirrer
64 Heater
64A Heater
64C Heater
66 O-ring
66A O-ring
66C O-ring
67 Snap ring
67A Snap ring
67C Snap ring
68 Bearing
68A Bearing
68C Bearing
69 Bearing spacer
69A Bearing spacer
69C Bearing spacer
70 Bearing
70A Bearing
70C Bearing
71 Snap ring
71A Snap ring
71C Snap ring
72 Pressurization media
72A Pressurization media
72C Pressurization media
74 Liquid sample
74A Liquid sample
74C Liquid sample
80 Lubricity tester
80A Lubricity tester
80C Lubricity tester
82B Gas tube
84B Piston
86B Sensor
88B Accumulator assembly

DESCRIPTION

Figure 1:
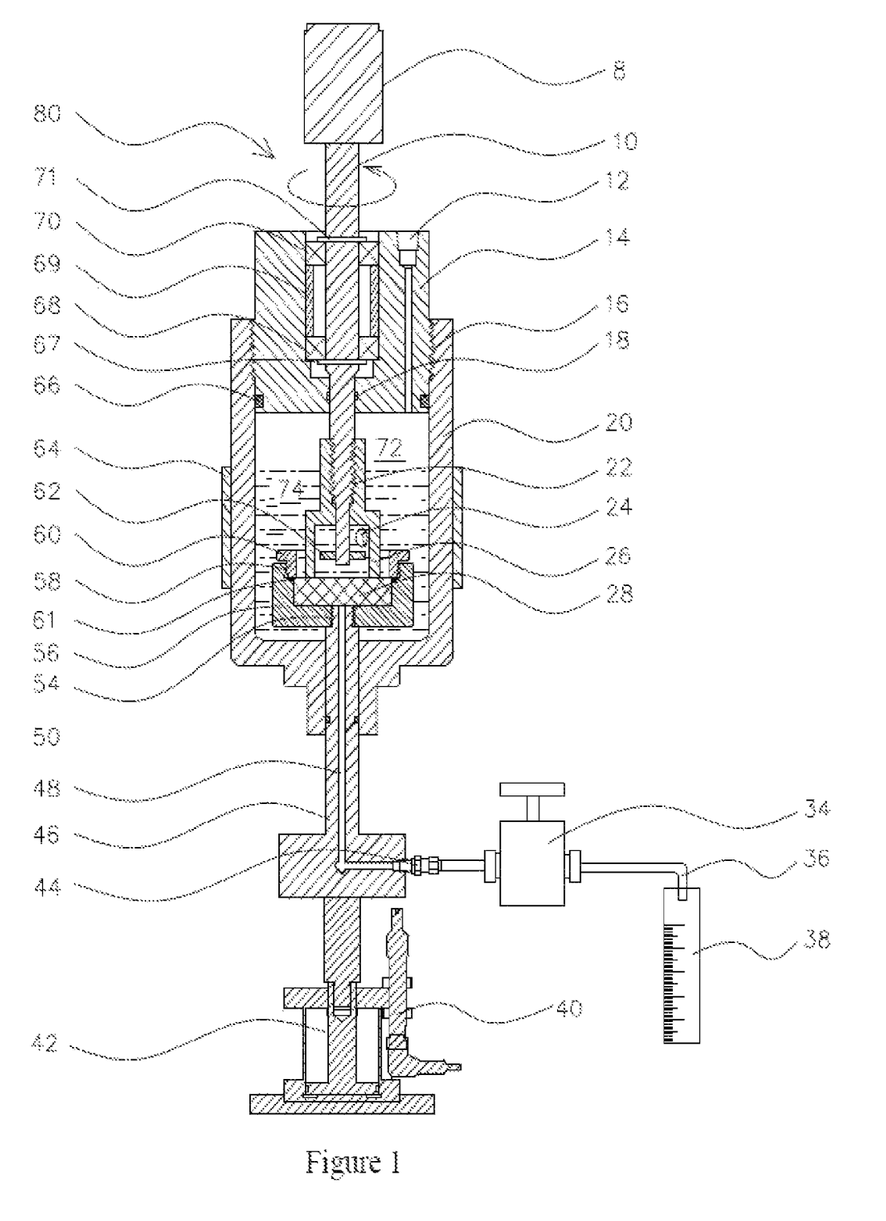
FIG. 1 is a cross-section view of lubricity tester 80 in the preferred embodiment of the invention.

FIG. 1—Preferred Embodiment

FIG. 1 is a cross-section view of a lubricity tester 80 with a cylindrical sample cup 20 and a bearing holder 14. Sample cup 20 is screwed onto bearing holder 14 via a thread 16. A top shaft 10 passes through the center of bearing holder 14, and is rotationally supported by a bearing 70, a bearing 68, a bearing spacer 69, a snap ring 67, and a snap ring 71. An o-ring 66 assures against leakage through thread 16. An o-ring 18 assures against leakage around top shaft 10.

A rotor 26, with a predominately ring shaped lower portion, is screwed onto the lower end of top shaft 10 via a thread 22. Thus rotor 26 can co-axially rotate together with top shaft 10. A stirrer 62 is fixed to the lower end of top shaft 10 and positioned inside rotor 26. Sample cup 20 is partially filled with a pressurization media 72 and a liquid sample 74. Liquid sample 74 submerges rotor 26 and is able to flow through rotor 26 through a hole 24. Pressurization media 72 is introduced through a pressurization port 12.

A solid sample 28, which typically can be a porous rock or a solid, non-porous metal, is placed inside a sample holder 56, which is attached to the top of a bottom shaft 46 via a thread 54. Solid sample 28 is secured to sample holder 56 by a retainer 60, which is screwed onto sample holder 56 via a thread 58. An O-ring 61 assures against leakage from thread 58. Liquid sample 74 saturates and infiltrates solid sample 28. Bottom shaft 46 extends downward through the bottom of sample cup 20 and an O-ring 50 provides assurance against leakage. A loading device 42 pushes bottom shaft 46 upward so that solid sample 28 presses against rotor 26, while the force applied on bottom shaft 46 is recorded, and the movement of bottom shaft 46 is recorded by a displacement sensor 40 as well.

A hole 48 in the center of bottom shaft 46 receives liquid sample 74 which has filtered through solid sample 28. Hole 48 extends downward though the length of bottom shaft 46 and is connected to a tube fitting 44. Tube fitting 44 connects to a valve 34, which is further connected to a tube 36 which drains into a receiver 38. Temperature control is provided by a heater 64 positioned radially outside the sample cup 20.

Operation—FIG. 1—Preferred Embodiment

In FIG. 1, to assemble lubricity tester 80, place o-ring 18 into bearing holder 14. Install bearing 68, bearing spacer 69, bearing 70, snap ring 67 and snap ring 71 onto top shaft 10. Insert top shaft 10 into bearing holder 14. Install stirrer 62 onto the lower end of top shaft 10. Screw rotor 26 onto top shaft 10 via thread 22. Install o-ring 66 onto bearing holder 14.

Install o-ring 50 onto bottom shaft 46, then insert bottom shaft 46 into the bottom of sample cup 20. Screw sample holder 56 onto the top of bottom shaft 46 via thread 54. Install solid sample 28 into sample holder 56 and install o-ring 61 onto sample holder 56 to assure against leakage between solid sample 28 and sample holder 56. Secure solid sample 28 by screwing retainer 60 into sample holder 56 via thread 58.

Pour liquid sample 74 into sample cup 20. Screw sample cup 20 onto bearing holder 14 via thread 16. Apply upward force at bottom of bottom shaft 46 using loading device 42, and displacement sensor 40 reads the movement of bottom shaft 46. Loading device 42 forces solid sample 28 to press tightly against rotor 26.

Connect tube fitting 44 to valve 34, and insert tube 36 into receiver 38. Inject pressurization media 72 through pressurization port 12. Adjust temperature as desired by activating heater 64. As top shaft 10 rotates, rotor 26 rotates and abrades against solid sample 28, causing the surface of solid sample 28 to wear away. As it does so, loading device 42 will move bottom shaft 46 up, while recording the upward force applied on bottom shaft 46. The power consumption and/or the torque value required to rotate shaft 10 is also recorded. Many means can be used to measure the torque on top shaft 10, such as the direct reading of a strain gauge on top shaft 10, the direct reading of torque from a motor 8 that drives top shaft 10, or the indirect reading of the power consumption of motor 8 that drives top shaft 10. The lubricity and/or the friction factor between solid sample 28 and rotor 26 is calculated from the torque on shaft 10 and the upward force applied to bottom shaft 46. The displacement sensor 40 records the changes as solid sample 28 is abraded.

Liquid sample 74 is able to saturate and infiltrate solid sample 28 by flowing through hole 24 in rotor 26. As liquid sample 74 is stirred by stirrer 62, pressurization media 72 forces it to filter through solid sample 28, whereupon it drains into hole 48, if solid sample 28 is porous. Valve 34 can be opened to allow liquid sample 74 to drain into receiver 38, allowing the measurement of the filtration value of solid sample 28 and liquid sample 74 under conditions of temperature and pressure.

Description

Figure 2:
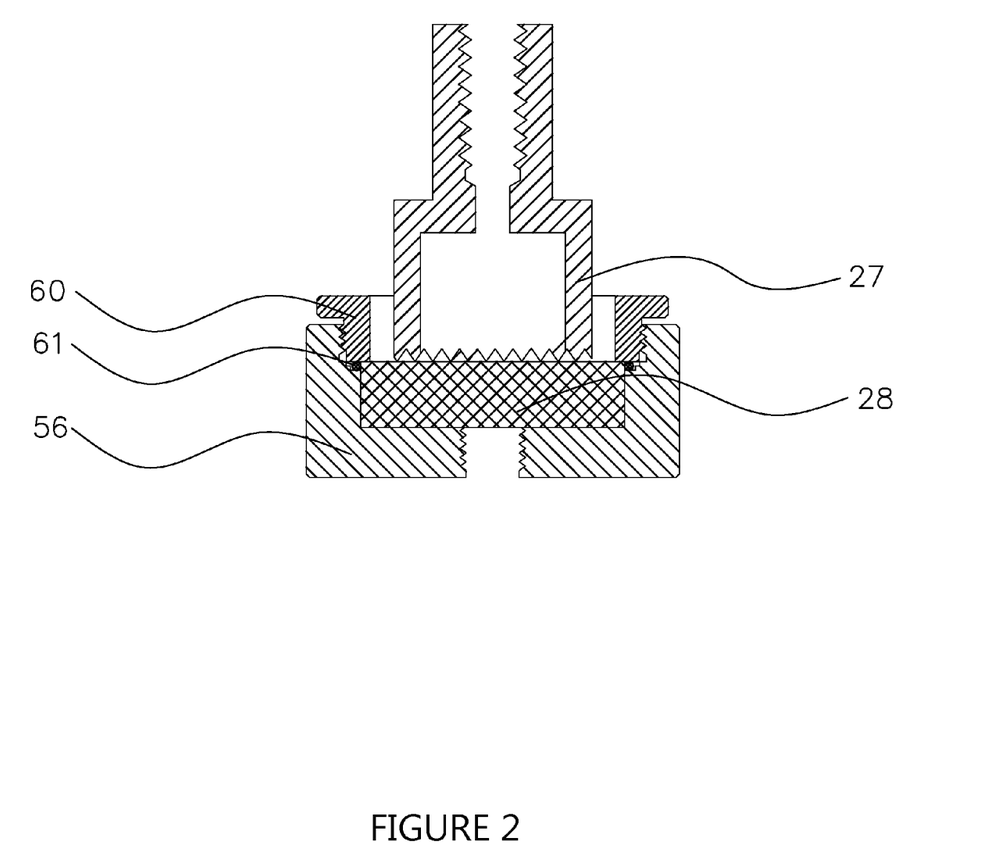
FIG. 2 is a detailed close-up of the rotor and sample assembly in FIG. 1, with a circular drill bit.

FIG. 2—Abrasive Circular Drill Bit Embodiment

FIG. 2 is a cross-section view of another configuration of FIG. 1, in which rotor 26 is replaced with an abrasive circular drill bit 27. Abrasive circular drill bit 27 is shaped to resemble a circular drill bit, as might be used in the petrochemical industry. This configuration would enable the simulation of real drilling processes under downhole conditions. It would also be capable of anticipating the penetration rate of a drill bit under downhole conditions.

Description

Figure 3:
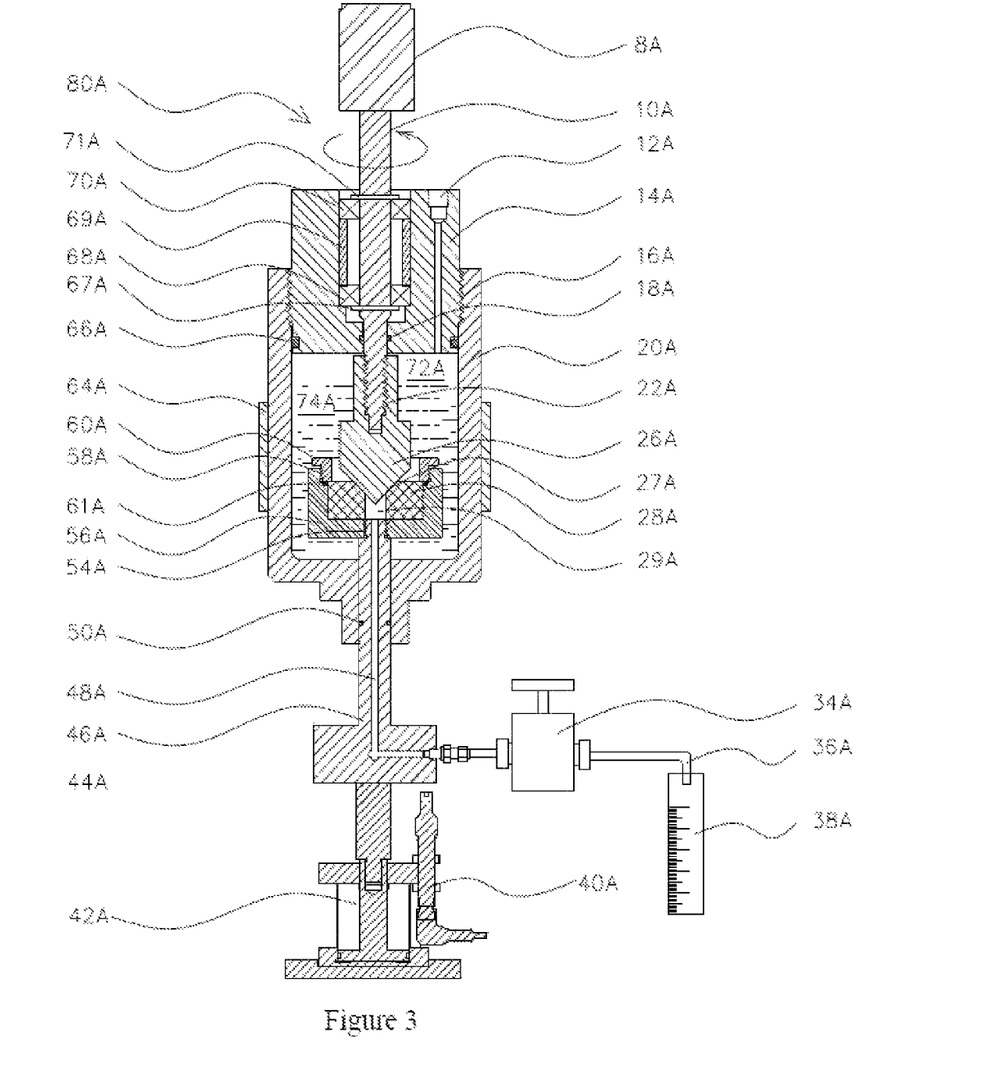
FIG. 3 is a cross-section view of lubricity tester 80B with a solid cone bit and a matching conical surface.

FIG. 3—Solid Cone Bit Embodiment

FIG. 3 is a cross-section view of a lubricity tester 80A with a sample cup 20A and a bearing holder 14A. Sample cup 20A is screwed onto bearing holder 14A via a thread 16A. An o-ring 66A assures against leakage through thread 16A. A top shaft 10A passes through the center of bearing holder 14A, and is rotationally supported by a bearing 70A, a bearing 68A, a bearing spacer 69A, a snap ring 67A, and a snap ring 71A. An o-ring 18A assures against leakage around top shaft 10A.

A solid cone bit 26A is screwed onto the lower end of top shaft 10A via a thread 22A. Sample cup 20A is partially filled with a pressurization media 72A and a liquid sample 74A. Liquid sample 74A submerges solid cone bit 26A. Pressurization media 72A is introduced through a pressurization port 12A.

A concave solid sample 28A with a central hole 29A and a conical surface 27A is placed inside a sample holder 56A, which is attached to the top of a bottom shaft 46A via a thread 54A. Concave solid sample 28A is secured to sample holder 56A by a retainer 60A, which is screwed onto sample holder 56A via a thread 58A. An o-ring 61A assures against leakage around concave solid sample 28A. Liquid sample 74A saturates and infiltrates concave solid sample 28A.

Bottom shaft 46A extends downward through the bottom of sample cup 20A, and an o-ring 50A provides assurance against leakage. Bottom shaft 46A is connected at the bottom to a loading device 42A and a displacement sensor 40A. Loading device 42A pushes bottom shaft 46A upward so that conical surface 27A in concave solid sample 28A fits around and presses against solid cone bit 26A.

A hole 48A receives liquid sample 74A which has filtered through concave solid sample 28A. Hole 48A extends downward through the length of bottom shaft 46A and is connected to a tube fitting 44A. Tube fitting 44A connects to a valve 34A, which is further connected to a tube 36A which drains into a receiver 38A. Temperature control is provided by a heater 64A positioned radially around the outside of sample cup 20A.

Operation—FIG. 3—Solid Cone Bit Embodiment

In FIG. 3, to assemble lubricity tester 80A, place o-ring 18A into bearing holder 14A. Install bearing 68A, bearing spacer 69A, bearing 70A, snap ring 67A and snap ring 71A onto top shaft 10A. Insert top shaft 10A into bearing holder 14A. Screw solid cone bit 26A onto top shaft 10A via thread 22A. Install o-ring 66A onto bearing holder 14A.

Install o-ring 50A onto bottom shaft 46A, then insert bottom shaft 46A into the bottom of sample cup 20A. Screw sample holder 56A onto the top of bottom shaft 46A via thread 54A. Install concave solid sample 28A into sample holder 56A. Install o-ring 61A onto sample holder 56A to assure against leakage between concave solid sample 28A and sample holder 56A. Secure concave solid sample 28A by screwing retainer 60A into sample holder 56A via thread 58A. Pour liquid sample 74A into sample cup 20A. Screw sample cup 20A onto bearing holder 14A via thread 16A. Apply upward force at bottom of bottom shaft 46A using loading device 42A, and displacement sensor 40A reads the movement of bottom shaft 46A. Loading device 42A forces concave solid sample 28A to press tightly against solid cone bit 26A.

Connect tube fitting 44A to valve 34A, and insert tube 36A into receiver 38A. Inject pressurization media 72A through pressurization port 12A. Adjust temperature as desired by activating heater 64A. As a motor 8A drives top shaft 10A rotating, solid cone bit 26A rotates and abrades against concave solid sample 28A, causing conical surface 27A of concave solid sample 28A to wear away. As it does so, loading device 42A will move bottom shaft 46A up. The displacement sensor 40A records the change. The lubricity and/or the friction factor between solid sample 28A and rotor 26A is calculated from the torque applied to shaft 10A and the upward force applied to bottom shaft 46A.

Liquid sample 74A is able to saturate and infiltrate concave solid sample 28A by submersion. Pressurization media 72A forces liquid sample 74A to filter through concave solid sample 28A and fill central hole 29A, whereupon it drains into hole 48A. Valve 34A can be opened to allow liquid sample 74A to drain into receiver 38A, allowing the measurement of the filtration value of concave solid sample 28A and liquid sample 74A under conditions of temperature and pressure.

Description

Figure 4:
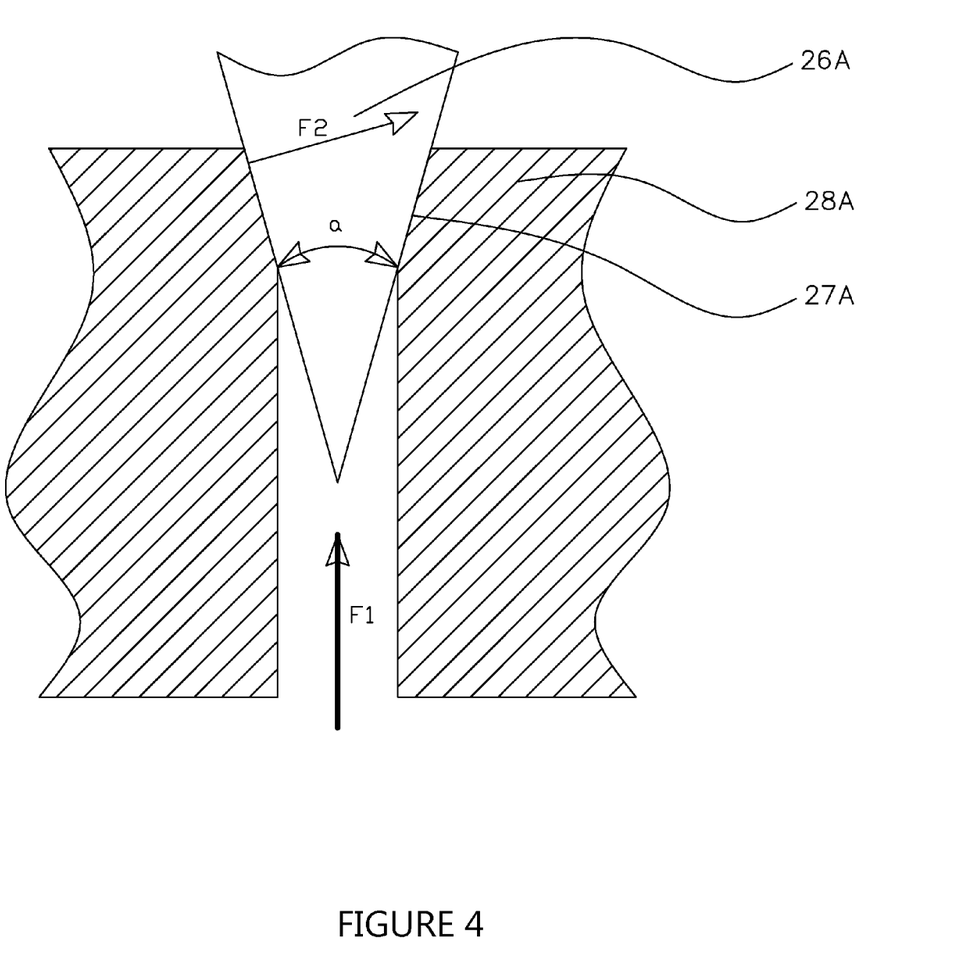
FIG. 4 is a detailed close-up of the rotor and sample assembly in FIG. 3.

FIG. 4—Detailed Close-Up of Solid Cone Bit 26A and Conical Surface 27A in FIG. 3

FIG. 4 is a detailed close-up of a solid cone bit 26A pressed against conical surface 27A on concave solid sample 28A. Solid cone bit 26A is shaped so that the angle of the cone corresponds exactly to the angle of conical surface 27A, thus the upward force used to press the concave solid sample 28A (F1) against the solid cone bit 26A generates a normal force (F2) on conical surface 27A. If the cone tip angle is α, then the relationship between (F1) and (F2) is:

$$F2 = F1/\sin(\tfrac{1}{2}\alpha)$$

When α is small, (F1) will produce a greatly-enhanced force (F2), requiring much less energy than would otherwise be necessary to produce a very high level of friction. This allows the solid cone bit 26A and the concave solid sample 28A to simulate down-hole conditions of pressure and friction which are much higher (and thus more analogous to realistic downhole conditions in a well being drilled) than they actually are, eliminating the necessity of applying those actual levels of energy or friction.

Description

Figure 5:
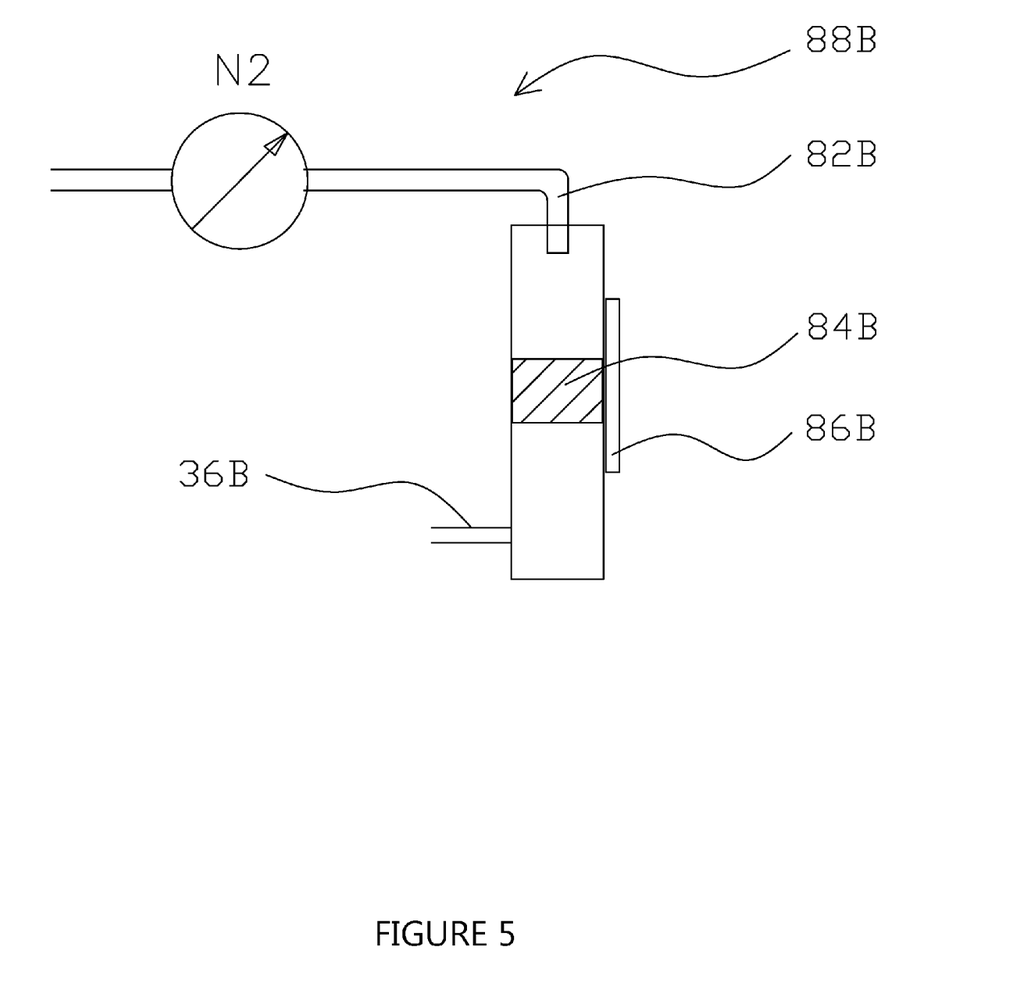
FIG. 5 is a detailed close-up of a back pressure accumulator assembly replacing the receiver in FIG. 1.

FIG. 5—Back Pressure Accumulator Assembly

FIG. 5 is a cross-section view of an a configuration in which the receiver 38 in FIG. 1 is replaced with an accumulator assembly 88B comprising a tube 36B which connects to the bottom area of an accumulator 88B and through which filtrate from sample 74 in FIG. 1 is introduced into accumulator assembly 88B. A sensor 86B detects the movement of a piston 84B as it rises and/or falls. A pressurization media source (in this illustration, nitrogen) is piped into the top area of accumulator assembly 88B via a gas tube 82B. Said nitrogen, in this figure, can provide back pressure for the operation of the lubricity tester.

Description

Figure 6:
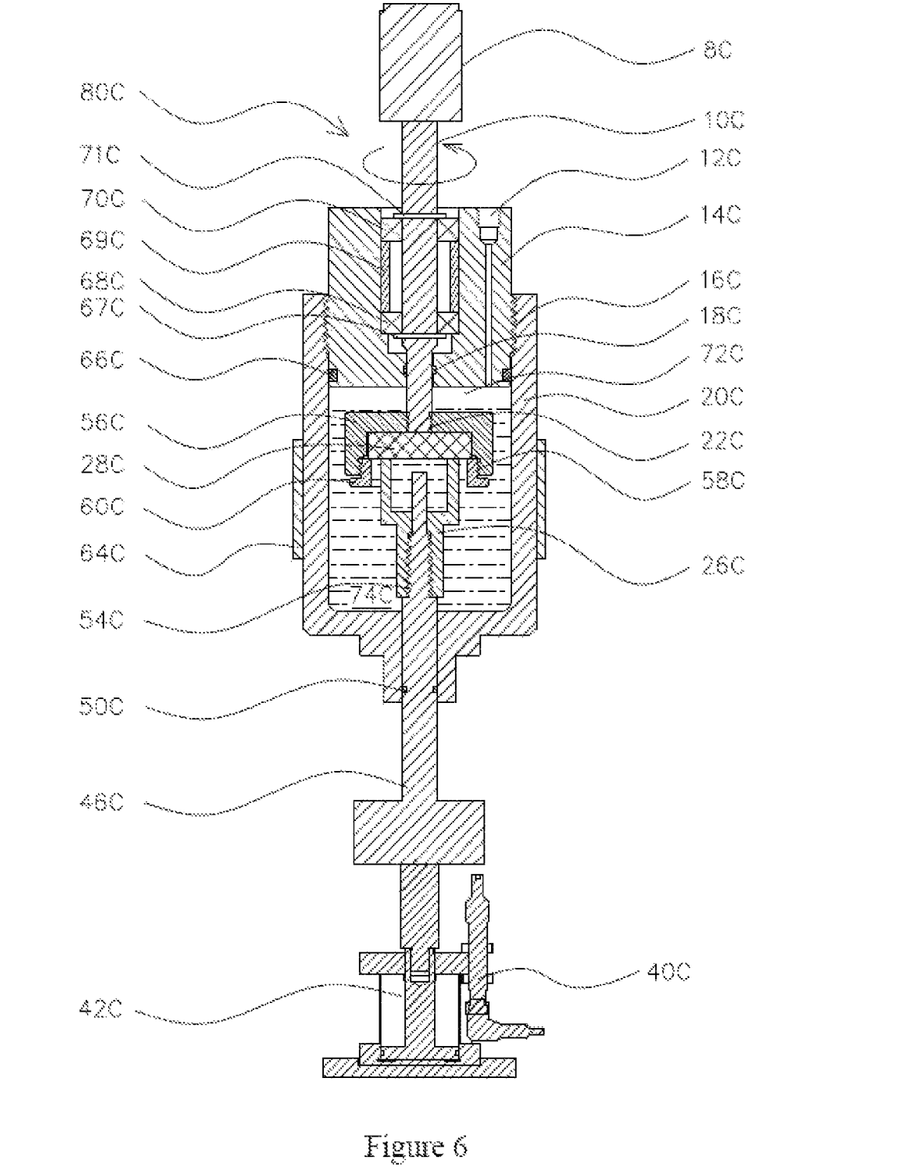
FIG. 6 is a cross-section view of the lubricity tester 80E with an rotating sample assembly.

FIG. 6—Inverted Rotor Assembly

FIG. 6 is a cross-section view of a lubricity tester 80C with a cylindrical sample cup 20C and a bearing holder 14C. Sample cup 20C is screwed onto bearing holder 14C via a thread 16C. A top shaft 100 passes through the center of bearing holder 14C, and is rotationally supported by a bearing 70C, a bearing 68C, a bearing spacer 69C, a snap ring 67C, and a snap ring 71C. An o-ring 66C assures against leakage through thread 16C. An o-ring 18C assures against leakage around top shaft 100.

A sample holder 56C is screwed onto the lower end of top shaft 100 via a thread 22C. A solid sample 28C, which typically can be a porous rock or a solid, non-porous metal, is placed up inside sample holder 56C and is secured to sample holder 56C by a retainer 60C, which is screwed onto sample holder 56C via a thread 58C.

A bottom shaft 46C extends up through the bottom of sample cup 20C. An o-ring 50C assures against leakage around bottom shaft 46C. A ring 26C is attached at the top of bottom shaft 46C via a thread 54C. Sample cup 20C is partially filled with a pressurization media 72C and a liquid sample 74C. Liquid sample 74C submerges ring 26C. Pressurization media 72C is introduced through a pressurization port 12C. Pressurization media 72C is introduced through a pressurization port 12C.

A loading device 42C pushes bottom shaft 46C upward so that ring 26C presses against solid sample 28C, and movement of bottom shaft 46C is recorded by a displacement sensor 40C. Temperature control is provided by a heater 64C positioned radially outside sample cup 20C.

Operation—FIG. 6—Inverted Rotor Assembly

In FIG. 6, to assemble lubricity tester 80C, place o-ring 18C into bearing holder 14C. Install bearing 68C, bearing spacer 69C, bearing 70C, snap ring 67C and snap ring 71C onto top shaft 100. Insert top shaft 10C into bearing holder 14C. Install o-ring 66C onto bearing holder 14C. Screw sample holder 56C onto the bottom of top shaft 100 via thread 22C. Install solid sample 28C into sample holder 56C and secure solid sample 28C by screwing retainer 60C into sample holder 56C via thread 58C.

Install o-ring 50C onto bottom shaft 46C, then insert bottom shaft 46C into the bottom of sample cup 20C. Screw ring 26C onto bottom shaft 46C via thread 54C.

Pour liquid sample 74C into sample cup 20C. Screw sample cup 20C onto bearing holder 14C via thread 16C. Loading device 42C will move bottom shaft 46C up, while recording the upward force applied on bottom shaft 46C. This will also push ring 26C upward against solid sample 28C. Inject pressurization media 72C through pressurization port 12C. Adjust temperature as desired by activating heater 64C.

As a motor 8C top shaft 10C rotating, sample holder 56C and solid sample 28C rotate and rub against ring 26C, causing the surface of solid sample 28C to wear away. As it does so, the power consumption and/or the torque value required to rotate shaft 10C is also recorded. The lubricity between solid sample 28C and ring 26C is calculated from the torque on shaft 10C and the upward force applied to bottom shaft 46C. The displacement sensor 40C records the changes as solid sample 28C is abraded.

Ramifications

In FIG. 1, solid sample 28 can be cylindrical or rectangular in shape.

In FIG. 1, because torque applied on rotor 26 equals the reaction torque applied on solid sample 28 which is further transferred to bottom shaft 46, torque measurement on bottom shaft 46 can be used to replace measurement of torque on top shaft 10.

In FIG. 1, pressurization media 72 can be either gas or liquid as long as the pressure is controlled.

In FIG. 1, the rotor 26 might be shaped like a standard drill bit or other shaped drill bits, as would be used in an oil well drilling process.

In FIG. 1, lubricity tester 80 might be operated at any angle, providing that rotor 26 and solid sample 28 are constantly submerged in liquid sample 74. This can be useful to simulate high-angle or horizontal drill conditions.

In FIG. 1, rotor 26 bottom can be shaped as a solid cylinder instead of a ring.

In FIG. 2, the circular drill bit 27 may be replaced by any other shaped drill bit, such as a conically threaded drill bit.

In FIG. 3, the solid cone bit 26A might be shaped like a standard drill bit, as would be used in an oil well.

In FIG. 3, lubricity tester 80A might be operated at any angle, providing that Solid cone bit 26B and concave solid sample 28A are constantly submerged in liquid sample 74A.

In FIG. 6, because torque applied on sample holder 56C and solid sample 28C equals the reaction torque applied on ring 26C which is further transferred to bottom shaft 46C, torque measurement on bottom shaft 46C can be used to replace measurement of torque on top shaft 100.

In FIG. 6, lubricity tester 80C might be operated at any angle, providing that ring 26C and solid sample 28C are constantly submerged in liquid sample 74C. This can be useful to simulate high-angle or horizontal drill conditions.

In FIG. 6, a hole in top shaft 100 could be provided to collect and measure filtrate through solid sample 28C.

In FIG. 6, ring 26C could be replaced with a conical, circular, or other shaped drill bit. In FIG. 6, solid sample 28C can be cylindrical or rectangular in shape.

CONCLUSION, AND SCOPE

Accordingly, the reader skilled in the art will see that this invention can be used to construct a high pressure vessel in which a solid and/or liquid sample can be tested under varying and controllable conditions of high pressure and high temperature conditions for lubricity and filtration capacity. In so doing, it satisfies an eminent drilling industry need.

Objects and Advantages

From the description above, a number of advantages of my lubricity tester become evident:
a. Due to limited number of components, current invention is easy to operate and maintain.
b. The pressure rating of current invention will only be limited to the pressure rating of its pressure vessel, tubing and valves, which can be up to 60,000 psi.
c. Current invention can test both fluids and solids dynamically and statically under high pressure and high temperature.
d. Current invention can test fluids and solids for both lubricity and filtration values under high pressure and high temperature.
e. The shape of both the rotor and the solid sample may be adapted to more closely approximate the shape of specific industrial features, such as drill bits, or other abrading hardware.

Further objects and advantages of my invention will become apparent from a consideration of the drawings and ensuing description.

What I claimed:
1. A lubricity testing device comprising:
 a) a pressure vessel partially filled with a liquid sample,
 b) a pressurization media is applied as a pressurization means to pressurize said liquid sample,
 c) a solid sample with a flattened surface, wherein said flattened surface of said solid sample is in contact with said liquid sample,
 d) a rotor with a ring shaped end that is in contact with said flattened surface of said solid sample, wherein said ring shaped end of said rotor rotationally abrades on said flattened surface of said solid sample around a longitudinal axis
 e) a means that pushes said flattened surface of said solid sample against said rotor in said longitudinal axial direction,
 f) a means to measure the force that said flattened surface of said solid sample pushes against said rotor in said longitudinal axial direction,
 g) a means to measure the torque to sustain said ring shaped end of said rotor, to rotationally abrades on said flattened surface of said solid sample.

2. The lubricity testing device of claim 1 further comprising a means to measure wear on said solid sample.

3. The lubricity testing device of claim 2 wherein said means to measure wear on said solid sample is a displacement sensor that measures the movement of said solid sample in said longitudinal axial direction.

4. The lubricity testing device of claim 1 wherein said solid sample is porous.

5. The lubricity testing device of claim 4 further comprising a means to measure a filtrate of said liquid sample passing through said solid sample.

6. The lubricity testing device of claim 1 wherein said pressurization media is a gas.

7. The lubricity testing device of claim 1 wherein said means to measure the torque is a motor from which power consumption can be indirectly read.

8. The lubricity testing device of claim 1 wherein said ring shaped end of said rotor rotationally abrades on said flattened surface of said solid sample is achieved by securing said solid sample and rotating said rotor.

9. The lubricity testing device comprising:
 a) a pressure vessel partially filled with a liquid sample,
 b) a pressurization media is applied as a pressurization means to pressurize said liquid sample,
 c) a solid sample with a concave surface, wherein said concave surface of said solid sample is in contact with said liquid sample,
 d) a rotor with a conical surface is pushed against said concave surface of said solid sample, wherein said conical surface of said rotor rotationally abrades on said concave surface of said solid sample,
 e) a means to measure the interactive force between said rotor and said solid sample,
 f) a means to measure applied torque that causes said conical surface of said rotor to rotationally abrades on said concave surface of said solid sample.

10. The lubricity testing device of claim 9 further comprising a means to provide thermal control of said pressure vessel.

11. The lubricity testing device of claim 9 further comprising a means to measure the wear on said solid sample.

12. The lubricity testing device of claim 11 wherein said means to measure wear on said solid sample is provided by a displacement sensor that measures the movement of solid sample in said longitudinal axial direction.

13. The lubricity testing device of claim 9 wherein said pressurization media is a gas.

14. The lubricity testing device of claim 9 wherein said rotor with said conical surface rotationally abrades on said concave surface of said solid sample is achieved by securing said solid sample and rotating said rotor.

15. The lubricity testing device of claim 9 wherein said means to measure the torque is a motor from which power consumption can be indirectly read.

\* \* \* \* \*